US 6,693,707 B2

(12) United States Patent
Kaneko

(10) Patent No.: US 6,693,707 B2
(45) Date of Patent: Feb. 17, 2004

(54) METHOD OF INSPECTING SURFACE-EMITTING SEMICONDUCTOR LASER AND INSPECTION DEVICE FOR SURFACE-EMITTING SEMICONDUCTOR LASER

(75) Inventor: Tsuyoshi Kaneko, Shimosuwa-machi (JP)

(73) Assignee: Seiko Epson Corporation, Tokyo (JP)

( * ) Notice: Subject to any disclaimer, the term of this patent is extended or adjusted under 35 U.S.C. 154(b) by 27 days.

(21) Appl. No.: 10/188,798

(22) Filed: Jul. 5, 2002

(65) Prior Publication Data

US 2003/0025091 A1 Feb. 6, 2003

(30) Foreign Application Priority Data

Jul. 10, 2001 (JP) ........................................ 2001-208892

(51) Int. Cl.[7] ............................................... G01N 21/00
(52) U.S. Cl. ................... 356/237.1; 356/237.2; 356/237.6; 356/635
(58) Field of Search ................... 356/237.1, 237.2, 356/237.5, 237.6, 635, 625

(56) References Cited

FOREIGN PATENT DOCUMENTS

| JP | 04294560 A | * 10/1992 | ........... H01L/21/66 |
| JP | A 2000-332355 | 11/2000 | |

* cited by examiner

Primary Examiner—Frank G. Font
Assistant Examiner—Roy M Punnoose
(74) Attorney, Agent, or Firm—Oliff & Berridge, PLC

(57) ABSTRACT

The present invention is a method of inspecting a surface-emitting semiconductor laser in which a resonator is formed in a vertical direction on a semiconductor substrate. The surface-emitting semiconductor laser to be inspected includes a pillar portion in at least part of the resonator, and this pillar portion includes an oxidized current blocking layer. The oxidized current blocking layer includes an oxide aperture, and an oxidized portion formed around the oxide aperture. The surface-emitting semiconductor laser is irradiated with laser light in a direction perpendicular to a surface of the semiconductor substrate from the side on which the pillar portion is disposed, and the shape of the oxide aperture is measured based on the amount of reflected light at the oxidized current blocking layer.

22 Claims, 2 Drawing Sheets

METHOD OF INSPECTING SURFACE-EMITTING SEMICONDUCTOR LASER AND INSPECTION DEVICE FOR SURFACE-EMITTING SEMICONDUCTOR LASER

Japanese Patent Application No. 2001-208892, filed on Jul. 10, 2001, is hereby incorporated by reference in its entirety.

BACKGROUND OF THE INVENTION

The present invention relates to a method of inspecting a surface-emitting semiconductor laser and an inspection device for a surface-emitting semiconductor laser.

A surface-emitting semiconductor laser is a light-emitting element capable of integration in two dimensions, whose application is a wide range of fields is anticipated, for example as a high-speed and large capacity light source for optical communications.

As a means of increasing the efficiency of a surface-emitting semiconductor laser, a current blocking structure has been proposed in which an AlAs layer or an AlGaAs layer having an extremely high content of aluminum is formed on a pillar portion formed on at least a part of a resonator, using the oxidized current blocking layer obtained by oxidizing this layer from the side, and is widely adopted. Such a current blocking layer is constructed from, for example, an oxide aperture formed from an AlAs layer, and an oxidized portion formed around this oxide aperture. This oxidized portion is formed from a layer including aluminum oxide. The layer including this aluminum oxide is formed by oxidizing an AlAs layer from the side. The diameter of the oxide aperture (also referred to below as the "oxide aperture diameter") forming this current blocking layer greatly affects the light emission efficiency of the element and the light emission pattern and the like, and therefore measurement of the diameter and shape of the oxide aperture is extremely important. Normally this current blocking layer is formed within an upper mirror forming the pillar portion. Alternatively, an active layer is formed at a lower portion of the upper mirror, and the current blocking layer is formed at a part of the upper mirror closer to the active layer.

On the other hand, as the semiconductor layer constituting the upper mirror is commonly used an AlGaAs material. However, the properties of this AlGaAs material are such that it absorbs light at visible wavelengths, and therefore attempts to confirm the diameter and shape of the oxide aperture using a conventional microscope or the like are difficult, because light is absorbed by the upper mirror, and the diameter and shape of the oxide aperture cannot easily be confirmed.

Here, there is the method of irradiating with infrared radiation passed by the AlGaAs material, to confirm the diameter of the oxide aperture. For example, Japanese Patent Application Laid-Open No. 2000-332355 discloses a method of measuring the oxide aperture diameter using an infrared radiation microscope.

However, an infrared source generates a large amount of heat, and therefore it is difficult to obtain a large light source, and in particular when the dispersion ratio is increased, since a sufficient quantity of light cannot be obtained, it is often difficult to obtain a clear image. Since the heights of the upper surface of the pillar portion and the oxidized current blocking layer are different, it is difficult to bring both of these into focus, and therefore accurate analysis of the diameter and shape of the oxide aperture is commonly not possible. Furthermore, not only is the wavelength of infrared radiation longer than that of visible light, but also a conventional infrared source such as a halogen lamp or the like includes a variety of wavelength components, and therefore the resolution of the image obtained is often low.

BRIEF SUMMARY OF THE INVENTION

The present invention may provide a method of inspecting a surface-emitting semiconductor laser and an inspection device for a surface-emitting semiconductor laser, enabling to accurately measure a diameter and shape of an oxide aperture.

Method of Inspecting Surface-emitting Semiconductor Laser

According to the present invention, there is provided a method of inspecting a surface-emitting semiconductor laser having a resonator which is formed in the vertical direction on a semiconductor substrate, wherein:

the surface-emitting semiconductor laser includes a pillar portion in at least a part of the resonator, the pillar portion having an oxidized current blocking layer which has an oxide aperture and an oxidized portion formed around the oxide aperture; and the surface-emitting semiconductor laser is irradiated with laser light from the side on which the pillar portion is formed, in a direction perpendicular to a surface of the semiconductor substrate to measure the shape of the oxide aperture based on the amount of reflected light from the oxidized current blocking layer.

The surface of the semiconductor substrate refers to a surface of the surface-emitting semiconductor laser on which the resonator is provided.

According to this inspection method, the shape of the oxide aperture is detected on the basis of the amount of reflected light obtained by irradiating the surface-emitting semiconductor laser with the laser light, so that the influence of noise components such as ambient light or the like is low, and therefore the shape of the oxide aperture can be accurately measured.

The method of inspecting a surface-emitting semiconductor laser may have following features (1) to (8).

(1) The shape of the oxide aperture may be measured on the basis of the difference between the amount of reflected light from the oxide aperture of the oxidized current blocking layer and the amount of reflected light from the oxidized portion of the oxidized current blocking layer.

(2) The laser light may have a wavelength shorter than the wavelength of light emitted by the surface-emitting semiconductor laser. In particular, when the diameter or shape of the oxide aperture is measured by measuring the difference between the amount of reflected light from the oxide aperture and the amount of reflected light from the oxidized portion, measurement is possible with a very small amount of reflected light. Therefore, measurement is possible even when a laser light of short wavelength is used and it is difficult to obtain a high intensity because the light is absorbed within the laser element. Since the resolving power can be increased by using the laser light of the shorter wavelength, the diameter or shape of the oxide aperture can be accurately measured.

(3) The laser light may be focused at a predetermined position of the oxidized current blocking layer by an optical element. This makes it possible to limit the amount of reflected light from unfocused portions such as light reflected from the surface of the semiconductor substrate, so that the diameter or shape of the oxide aperture can be measured even more accurately.

(4) Two-dimensional scanning may be done for the laser light reflected by at least a cross-section of the pillar portion in a plane parallel to the surface of the semiconductor substrate. This makes it possible to accurately determine the entire shape of the oxidized current blocking layer.

In this case, two-dimensional scanning may be done for the laser light reflected by a region which is larger than the cross-section of the pillar portion and includes the cross-section of the pillar portion in the plane parallel to the surface of the semiconductor substrate. This makes it possible to more accurately determine the shape of the oxidized current blocking layer in the resonator.

(5) Two-dimensional scanning may be done for the laser light reflected by a plane parallel to the surface of the semiconductor substrate; the distance between the surface-emitting semiconductor laser and the optical element being used to focus the laser light may be varied; and the distance may be fixed at a point at which the difference between the amount of reflected light from the oxidized portion and the amount of reflected light from the oxide aperture is maximum to measure the amounts of reflected light. This makes it possible to accurately focus on a predetermined position of the oxidized current blocking layer. By irradiating the laser light and capturing the difference in the amount of the reflected lights as data, the influence of noise components such as ambient light or the like is low, and the diameter or shape of the oxide aperture can be yet more accurately measured. In this case, even if the amount of the reflected lights obtained is very little, as long as the difference between the amount of the reflected lights of the oxidized portion and the oxide aperture can be determined, the diameter or shape of the oxide aperture can be measured, and therefore a high output light source is not required.

(6) A two-dimensional distribution of the amount of reflected light may be obtained on the basis of the position of the two-dimensional scanning of the laser light and the amount of the reflected light. This make it possible to determine the diameter or shape of the oxide aperture.

(7) The surface-emitting semiconductor laser may be an element in the process of formation. The element in the process of formation refers to an element which is at a stage before the completion of the surface-emitting semiconductor laser. That is to say, according to the present invention, even if the surface-emitting semiconductor laser is an element in the process of formation, as long as the element includes a pillar portion in at least part of the resonator, and the pillar portion includes an oxidized current blocking layer having the above described oxide aperture and oxidized portion, then the above described effect and benefit can be obtained.

In this case, no electrode through which a current is injected into an active layer may be formed in the element. In this configuration, the influence of light reflected from the electrodes can be eliminated, so the diameter and shape of the oxide aperture can be accurately measured.

(8) The surface-emitting semiconductor laser may be moved to a predetermined position by moving a test piece stage in a direction parallel to the surface of the semiconductor substrate, after the position of the surface-emitting semiconductor laser in a plane parallel to the surface of the semiconductor substrate is confirmed before the laser light irradiation is performed.

Inspection Device for a Surface-emitting Semiconductor Laser

According to the present invention, there is provided an inspection device for a surface-emitting semiconductor laser having a resonator which is formed in the vertical direction on a semiconductor substrate, wherein the surface-emitting semiconductor laser includes a pillar portion in at least a part of the resonator, the pillar portion having an oxidized current blocking layer which has an oxide aperture and an oxidized portion formed around the oxide aperture; and wherein the inspection device includes:
a test piece stage on which is mounted the surface-emitting semiconductor laser to be inspected;
a movement mechanism which moves the test piece stage in a direction parallel to a surface of the semiconductor substrate to adjust the position of the surface-emitting semiconductor laser in a plane parallel to the surface of the semiconductor substrate;
a laser light source which irradiates the surface-emitting semiconductor laser with laser light from the side on which the pillar portion is disposed in a direction perpendicular to the surface of the semiconductor substrate;
an optical element which focuses the laser light;
a distance adjustment section which adjusts the distance between the surface-emitting semiconductor laser and the optical element;
a scanning section which performs two-dimensional scanning of the laser light reflected by a plane parallel to the surface of the semiconductor substrate; and
a measurement section which measures the amount of reflected light from an object irradiated with the laser light.

According to this inspection device, the shape of the oxide aperture can be accurately measured.

This inspection device for a surface-emitting semiconductor laser may have following features (1) to (8).

(1) The measurement section may measure the amount of reflected light from the oxide aperture of the oxidized current blocking layer and the amount of reflected light from the oxidized portion of the oxidized current blocking layer.

(2) The inspection device for a surface-emitting semiconductor laser may further comprise:
an analysis section which obtains a two-dimensional distribution of the amount of reflected light; and
a display section which displays the two-dimensional distribution obtained by the analysis section.

(3) The scanning section may perform two-dimensional scanning of the laser light reflected by the plane parallel to the surface of the semiconductor substrate, while the distance adjustment section may vary the distance between the surface-emitting laser and the optical element, and the distance adjustment section may fix the distance at a point at which the difference between the amount of reflected light from the oxidized portion and the amount of reflected light from the oxide aperture is maximum.

(4) The laser light from the laser light source may have a wavelength shorter than the wavelength of light emitted by the surface-emitting semiconductor laser.

(5) The scanning section may perform two-dimensional scanning of the laser light reflected by at least a cross-section of the pillar portion in the plane parallel to the surface of the semiconductor substrate.

In this case, the scanning section may perform two-dimensional scanning of the laser light reflected by a region which is larger than the cross-section of the pillar portion and includes the cross-section of the pillar portion in the plane parallel to the surface of the semiconductor substrate.

(6) The surface-emitting semiconductor laser may be an element in the process of formation.

In this case, no electrode through which a current is injected into an active layer may be formed in the element.

(7) The analysis section may obtain a two-dimensional distribution of the amount of reflected light based on the position of the scanning of the laser light caused by the scanning section and the amount of the reflected light measured by the measurement section.

(8) The inspection device for a surface-emitting semiconductor laser may further comprise a position detection section which confirms the position of the surface-emitting semiconductor laser in the plane parallel to the surface of the semiconductor substrate, wherein the movement mechanism may move the surface-emitting semiconductor laser to a predetermined position by moving the test piece stage based on information from the position detection section.

DETAILED DESCRIPTION OF THE EMBODIMENT

Figure 1:
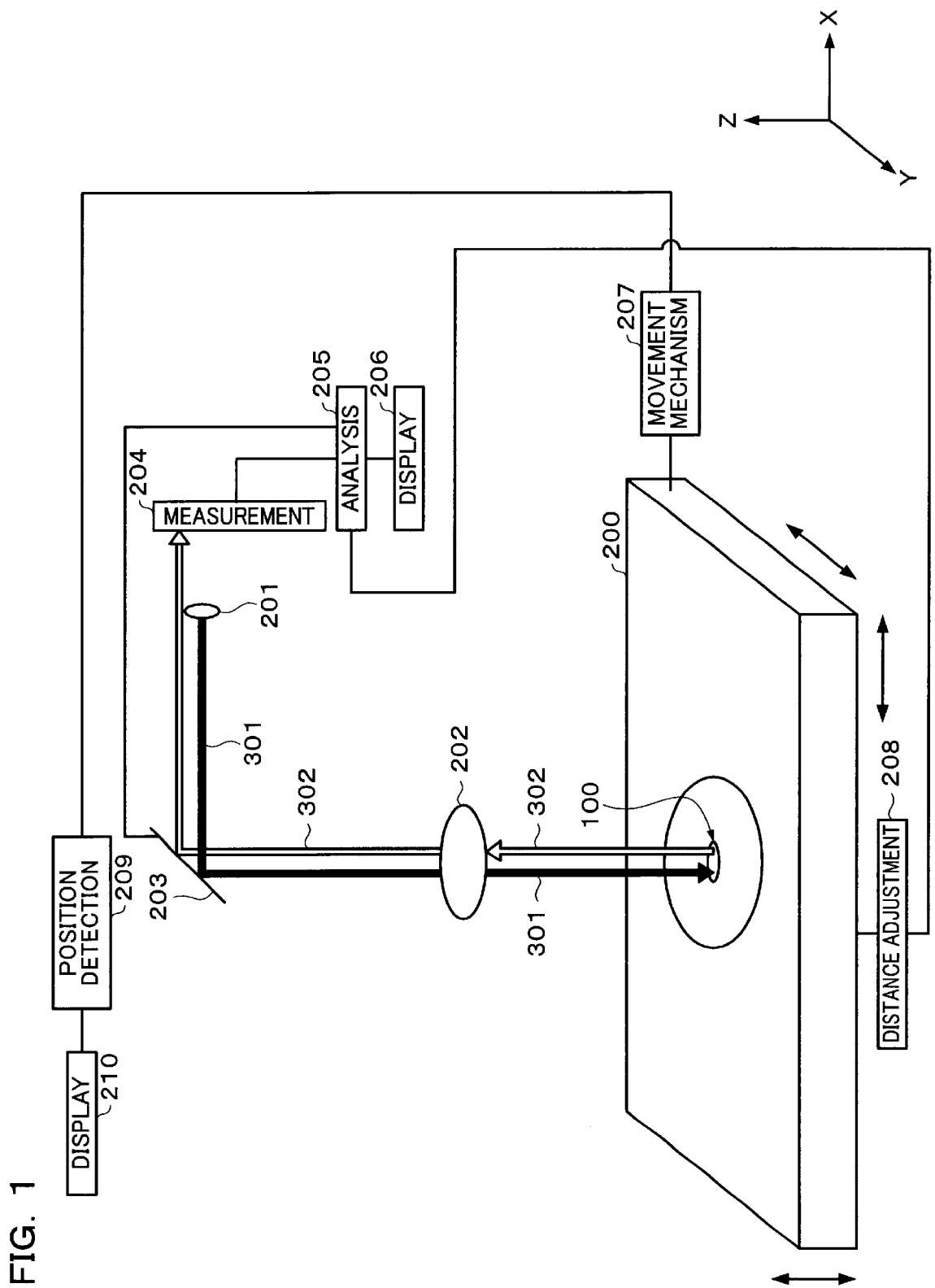
FIG. 1 schematically shows an inspection device for a surface-emitting semiconductor laser according to one embodiment of the present invention.
Figure 2:
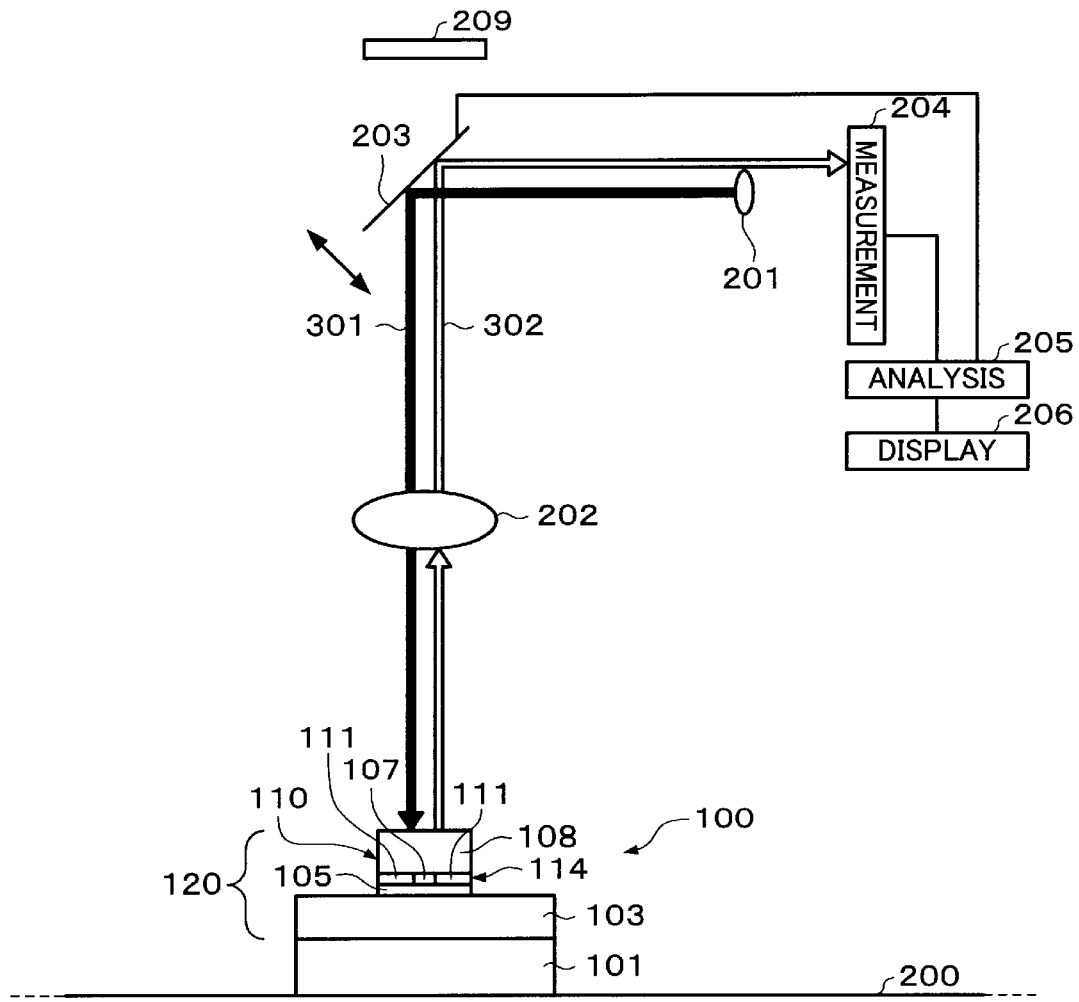
FIG. 2 is a diagram schematically showing part of the inspection device shown in FIG. 1, and is an enlarged view of a portion of the surface-emitting semiconductor laser to be inspected.

Embodiment of the present invention will be described with reference to the drawings.
Configuration of Surface-emitting Laser FIG. 1 is a figure showing schematically one embodiment of the inspection device for a surface-emitting semiconductor laser 100 of the present invention. FIG. 2 is a figure showing schematically a part of the inspection device shown in FIG. 1, and is an enlarged view of a part of the surface-emitting semiconductor laser 100 to be inspected.

First, the configuration of the surface-emitting semiconductor laser (hereinafter also referred to as "surface-emitting laser") 100 to be inspected is described. The surface-emitting laser 100, as shown in FIG. 2, includes a vertical resonator (hereinafter also referred to as a "resonator") 120, formed on a semiconductor substrate 101. The resonator 120 is formed by lamination in sequence on the semiconductor substrate 101 of a lower mirror 103, and active layer 105, and an upper mirror 108. Between the semiconductor substrate 101 and the resonator 120, a buffer layer (not shown in the drawings) of n-type GaAs is formed.

The lower mirror 103 is formed on the n-type buffer layer, and is formed as a distributed reflection type multilayer mirror of 30 pairs of alternately laminated n-type $Al_{0.85}Ga_{0.15}As$ and n-type $Al_{0.15}Ga_{0.85}As$ layers. The active layer 105 is formed on the lower mirror 103, including GaAs well layers and $Al_{0.3}Ga_{0.7}As$ barrier layers, and the well layers have a multi-well structure formed of three layers. The upper mirror 108 is formed on the active layer 105, and is formed as a distributed reflection type multilayer mirror of 25 pairs of alternately laminated p-type $Al_{0.85}Ga_{0.15}As$ and p-type $Al_{0.15}Ga_{0.85}As$ layers. Above and below the active layer 105 are respectively formed an n-type cladding layer of n-type $Al_{0.5}Ga_{0.5}As$ and a p-type cladding layer of $Al_{0.5}Ga_{0.5}As$ (neither shown in the drawings).

The upper mirror 108 is of p-type by zinc doping, and the lower mirror 103 is of n-type by silicon doping. Therefore, the upper mirror 108, the active layer 105 doped with no impurity, and the lower mirror 103 form a pin diode.

A pillar-shaped semiconductor deposition body (pillar portion) 110 is formed on the resonator 120. The pillar portion 110 is formed by etching a portion of the resonator 120 extending from the laser light emission side of the surface emission type light-emitting element 100 to an intermediate part of the lower mirror 103 to a circular shape as seen from the direction of laser light emission. In this embodiment, the plan form of the pillar portion 110 is described as circular, but the plan form of the pillar portion 110 can be an arbitrary shape. Here, the pillar portion 110 refers to a part of the resonator 120, being a pillar-shaped semiconductor deposition body including at least the upper mirror 108, a current blocking layer 114, and the active layer 105. Furthermore, in the pillar portion 110, on the upper mirror 108 a contact layer (not shown in the drawings) of p-type GaAs is formed.

The current blocking layer 114 is formed for the purpose of efficient injection of a current into the active layer 105. This current blocking layer 114 includes an oxide aperture 107 formed of a p-type AlAs layer, for example, and an oxidized portion 111 formed on the periphery of this oxide aperture 107. To form this current blocking layer 114, close to the active layer 105 within the upper mirror 108, an AlAs layer is previously formed, and this AlAs layer is exposed from the side to an atmosphere of steam at approximately 400° C. By means of this process, this AlAs layer is oxidized, and as a result the oxidized portion (portion including aluminum oxide) forms the oxidized portion 111, and the portion left unoxidized forms the oxide aperture 107. That is to say, in this process, the AlAs layer is oxidized from the periphery toward the interior, and the insulating aluminum oxide is formed, forming the oxidized portion 111 including this aluminum oxide.

As described above, the diameter and form of this oxide aperture 107 greatly affects the light emission efficiency of the element, the light emission pattern and so on, and therefore measuring the diameter and shape of the oxide aperture 107 is extremely important. In this embodiment of the inspection device for the surface-emitting laser 100, description is made of an example of this measuring of the diameter and shape of the oxide aperture 107.

It should be noted that in this embodiment, the surface-emitting laser 100 to be inspected is shown as an element in the process of being formed. More specifically, in this embodiment, the surface-emitting laser 100 to be inspected is shown as an element before the pair of electrodes for injecting a current into the active layer 105 is formed. By carrying out the inspection on the element in this state, measurement can be made without the influence of light reflected from the electrodes, and therefore the diameter and shape of the oxide aperture 107 can be accurately measured. When the method of inspection of this embodiment is applied to the surface-emitting laser 100 is not particularly restricted, as long as it is after the oxidized current blocking layer 114 is formed on the pillar portion 110.

After the diameter and shape of the oxide aperture 107 of the surface-emitting laser 100 shown in FIG. 1 is measured by this embodiment of the method of inspection, by a well-known manufacturing process the pair of electrodes for injecting a current into the active layer 105 is formed. By means of this electrode formation process, a drivable surface-emitting laser is obtained.
Inspection Device for Surface-emitting Laser Next, the inspection device for the surface-emitting laser 100 of this embodiment is described.

As shown in FIGS. 1 and 2, the inspection device of this embodiment includes a test piece stage 200, a movement mechanism 207 which moves this test piece stage 200, a laser light source 201, an optical element 202 which focuses the laser light, a distance adjustment section 208 which adjusts the distance between the surface-emitting laser 100 and the optical element 202, a scanning section 203 which two-dimensionally scans the laser light 301 reflected by a plane parallel to the surface of the semiconductor substrate 101, a measurement section 204 which measures the amount of reflected light 302 from the object irradiated with the laser light 301, an analysis section 205 which constructs the two-dimensional distribution of the amount of reflected light measured by the measurement section 204, and a display section 206 which displays the two-dimensional distribution of the reflected light. In this embodiment, the surface of the semiconductor substrate 101 is parallel to the X-Y plane in FIG. 1.

The test piece stage 200 is a stage on which the surface-emitting laser 100 to be inspected is mounted, and as shown in FIG. 2, the surface-emitting laser 100 is mounted with the rear surface (the surface opposite to that on which the resonator 120 is formed) of the semiconductor substrate 101 in contact with the test piece stage 200.

The movement mechanism 207, as shown in FIG. 2, is adapted to move the test piece stage 200 in a direction parallel to the surface of the semiconductor substrate 101, that is to say, in a direction parallel to the X-Y plane in FIG. 1. In the inspection device of this embodiment, the movement mechanism 207 has functions to move the test piece stage 200 in directions parallel to each of the X-direction and Y-direction. In the movement mechanism 207, movement of the test piece stage 200 can be carried out manually or automatically. By moving the test piece stage 200 in this way, the position of the surface-emitting laser 100 in a plane parallel to the X-Y plane can be adjusted.

In this embodiment of the inspection device, furthermore, as shown in FIG. 1, a position detection section 209 is formed in order to check the position of the surface-emitting laser 100 in a plane parallel to the surface of the semiconductor substrate 101. The position detection section 209 images the surface-emitting laser 100 to be inspected, and is provided in order to be able to confirm the position of the surface-emitting laser 100 in a plane parallel to the X-Y plane in FIG. 1. As the position detection section 209 may be used, for example, a CCD camera. The image captured by the position detection section 209 is shown on a display section 210, being for example a display.

Based on information from this position detection section 209, the movement mechanism 207 moves the test piece stage 200 in respective directions parallel to the X-direction and Y-direction, in order to position the surface-emitting laser 100 at a predetermined position.

The laser light source 201 irradiates the surface-emitting laser 100 with laser light 301 from the side on which the pillar portion 110 is formed, in the direction perpendicular to the surface of the semiconductor substrate 101. As the laser light 301 can be used a single wavelength. By determining the shape of the oxide aperture 107 from the amount of reflected light obtained from irradiating the surface-emitting laser 100 with the single-wavelength laser light 301, a clear image of the current blocking layer 114 can be obtained, which is less susceptible to the influence of noise components such as ambient light or the like, and from which the inspection result can be obtained. As a result, the diameter and shape of the oxide aperture 107 can be accurately measured.

When an electrode is formed in the surface-emitting laser 100 and then the surface-emitting laser 100 is driven, the laser light 301 emitted from this laser light source 201 may have a wavelength shorter than the wavelength of the laser light emitted by the surface-emitting laser. That is to say, in this embodiment, since the diameter and shape of the oxide aperture 107 is measured based on the difference between the amount of reflected light from the oxide aperture 107 and the amount of reflected light from the oxidized portion 111, the measurement is possible with even only a very small amount of reflected light. Therefore, even if a laser light of short wavelength is used, which is absorbed within the surface-emitting laser 100, and for which a high intensity is difficult to obtain, even so the measurement is possible. Since by using a laser light of short wavelength the resolving power can be increased, the diameter and shape of the oxide aperture 107 can be accurately measured. For example, in this embodiment, for the laser light 301, a laser light of wavelength 650 nm can be used.

The optical element 202 functions to focus the laser light 301. In the inspection device of this embodiment, it functions to focus the laser light 301 emitted by the laser light source 201 on the cross-section of the oxidized current blocking layer 114.

The distance adjustment section 208 adjusts the distance between the surface-emitting laser 100 and the optical element 202. In the inspection device of this embodiment, the scanning section 203 performs two-dimensional scanning of the laser light 301 reflected by a plane parallel to the surface of the semiconductor substrate 101, while the distance adjustment section 208 varies the distance between the surface-emitting laser 100 and the optical element 202, and the distance adjustment section 208 fixes the distance at the point at which the difference between the amount of reflected light from the oxidized portion 111 and the amount of reflected light from the oxide aperture 107 is maximum.

The scanning section 203 carries out two-dimensional scanning of the laser light 301 reflected by a plane parallel to the X-Y plane in FIG. 1. As an example of the scanning section 203 can be cited a galvano-scanner. In this embodiment, the scanning section 203 carries out two-dimensional scanning of the laser light 301 reflected by at least the part of a plane parallel to the X-Y plane in FIG. 1 that is the cross-section of the pillar portion 110. Furthermore, in order to confirm the shape of the resonator 120 itself, the scanning section 203 carries out two-dimensional scanning of the laser light 301 reflected by part of a plane parallel to the X-Y plane in FIG. 1 including the cross-section of the pillar portion 110, and larger than the cross-section.

The measurement section 204 measures the amount of reflected light from the test piece irradiated by the laser light 301.

The analysis section 205 obtains a two-dimensional distribution based on the amount of reflected light from the test piece irradiated by the laser light 301. The analysis section 205 of the inspection device of this embodiment, as shown in FIG. 1, obtains a two-dimensional distribution of the amount of reflected light based on the position of the laser light 301 scanned by the scanning section 203 and the amount of reflected light measured by the measurement section 204.

The display section 206 displays the two-dimensional distribution obtained by the analysis section 205. As the display section 206 may be cited, for example, a display.

Method of Inspecting Surface-emitting Laser

Next, a method of inspecting the surface-emitting laser 100 of this embodiment using the inspection device shown in FIGS. 1 and 2 is described.

First, the surface-emitting laser 100 is mounted on the test piece stage 200. At this time, the surface-emitting laser 100 is mounted with the semiconductor substrate 101 toward the test piece stage 200. Next, using the position detection section 209 shown in FIG. 1, the position of the surface-emitting laser 100 to be inspected is confirmed, and based on information from this position detection section 209, using the movement mechanism 207 as required, the test piece stage 200 is moved in the X-direction and Y-direction, so that the surface-emitting laser 100 is centered in the imaging area. Next, laser light 301 is emitted from the laser light source 201.

Next, the scanning section 203 is caused to perform two-dimensional scanning of the laser light 301 reflected by a plane parallel to the X-Y plane in FIG. 1, while using the distance adjustment section 208, the distance between the surface-emitting laser 100 and the optical element 202 is varied. In the inspection device of this embodiment, this distance is fixed at the point at which the difference between the amount of reflected light from the oxidized portion 111 and the amount of reflected light from the oxide aperture 107 in the current blocking layer 114 of the surface-emitting laser 100 is maximum, and the measurement section 204 is used to measure the amounts of reflected light. By this method, accurate focusing at a predetermined position of the oxidized current blocking layer 114 is possible.

Furthermore, based on the position of the scanning of the laser light 301 performed by the scanning section 203 and the amount of reflected lights measured by the light measurement section 204, the analysis section 205 obtains a two-dimensional distribution of the amount of reflected light. This two-dimensional distribution is displayed by the display section 206. From this distribution, the diameter and shape of the oxide aperture 107 can be determined.

Effect and Benefit

According to the method of inspection of the surface-emitting laser 100 and inspection device of this embodiment, the laser light 301 is irradiated, and the difference in the amount of reflected light is obtained as data, whereby the susceptibility to the influence of noise components such as ambient light or the like is reduced, and a clear image can be obtained. In this, even with a very small amount of reflected light, as long as the difference between the amount of reflected light from the oxidized portion 111 and the amount of reflected light from the oxide aperture 107 can be detected, the diameter and suchlike of the oxide aperture 107 can be measured, and therefore a high output light source is not required. The laser light with which the surface-emitting laser 100 is irradiated may have a wavelength shorter than the wavelength of the laser light emitted by the surface-emitting laser 100.

Since the laser light 301 is focused on the oxidized current blocking layer 114 using the optical element 202, the resolution of the image of the oxidized current blocking layer 114 can be improved. Since the laser light 301 is focused in a predetermined position of the oxidized current blocking layer 114, the amount of reflected light from the unfocused portion, light reflected from the surface of the semiconductor substrate 101 and the like, can be limited, as a result of which the diameter and shape of the oxide aperture 107 can be accurately measured.

By causing the scanning section 203 to perform two-dimensional scanning of the laser light 301 reflected by at least the cross-section of the pillar portion 110 in a plane parallel to the surface of the semiconductor substrate 101 (the X-Y plane in FIG. 1), the overall form of the oxidized current blocking layer 114 can be determined accurately. By carrying out two-dimensional scanning of the laser light 301 reflected by a region which is larger than the cross-section of the pillar portion 110 and includes the cross-section of the pillar portion 110, in the plane parallel to the surface of the semiconductor substrate 101 (the X-Y plane in FIG. 1), the overall form of the oxidized current blocking layer 114 occupying the whole resonator 120 can be accurately determined.

Moreover, accurate focusing on the oxidized current blocking layer 114 is possible by causing the scanning section 203 to perform two-dimensional scanning of the laser light 301 emitted from the laser light source 301 and reflected by the plane parallel to the surface of the semiconductor substrate 101, causing the distance adjustment section 208 to vary the distance between the surface-emitting laser 101 and the optical element 202 and to fix this distance at the point at which the difference between the amount of reflected light from the oxidized portion 111 and the amount of reflected light from the oxide aperture 107 is a maximum.

It should be noted that interchanging the p-type and n-type characteristics of the semiconductor layers in the above described embodiments does not depart from the essence of the present invention. In the above described embodiments, the description is of an AlGaAs type, but depending on the wavelength to be generated, other materials, such as for example GaInNAs type, GaAsSb type, GaInP type, and suchlike semiconductor materials can be used.

Although a surface-emitting laser having a single pillar portion is shown in the above embodiment, there may be a plurality of pillar portions on a single substrate.

What is claimed is:

1. A method of inspecting a surface-emitting semiconductor laser having a resonator which is formed in the vertical direction on a semiconductor substrate, wherein:
   the surface-emitting semiconductor laser includes a pillar portion in at least a part of the resonator, the pillar portion having an oxidized current blocking layer which has an oxide aperture and an oxidized portion formed around the oxide aperture; and
   the surface-emitting semiconductor laser is irradiated with laser light from the side on which the pillar portion is formed, in a direction perpendicular to a surface of the semiconductor substrate to measure the shape of the oxide aperture based on the amount of reflected light from the oxidized current blocking layer.

2. The method of inspecting a surface-emitting semiconductor laser as defined in claim 1,
   wherein the shape of the oxide aperture is measured on the basis of the difference between the amount of reflected light from the oxide aperture of the oxidized current blocking layer and the amount of reflected light from the oxidized portion of the oxidized current-blocking layer.

3. The method of inspecting a surface-emitting semiconductor laser as defined in claim 1,
   wherein the laser light has a wavelength shorter than the wavelength of light emitted by the surface-emitting semiconductor laser.

4. The method of inspecting a surface-emitting semiconductor laser as defined in claim 1,
   wherein the laser light is focused at a predetermined position of the oxidized current blocking layer by an optical element.

5. The method of inspecting a surface-emitting semiconductor laser as defined in claim 1,
   wherein two-dimensional scanning is done for the laser light reflected by at least a cross-section of the pillar portion in a plane parallel to the surface of the semiconductor substrate.

6. The method of inspecting a surface-emitting semiconductor laser as defined in claim 5,
   wherein two-dimensional scanning is done for the laser light reflected by a region which is larger than the cross-section of the pillar portion and includes the cross-section of the pillar portion in the plane parallel to the surface of the semiconductor substrate.

7. The method of inspecting a surface-emitting semiconductor laser as defined in claim 4, wherein:
two-dimensional scanning is done for the laser light reflected by a plane parallel to the surface of the semiconductor substrate;
the distance between the surface-emitting semiconductor laser and the optical element being used to focus the laser light is varied; and
the distance is fixed at a point at which the difference between the amount of reflected light from the oxidized portion and the amount of reflected light from the oxide aperture is maximum to measure the amounts of reflected light.

8. The method of inspecting a surface-emitting semiconductor laser as defined in claim 5,
wherein a two-dimensional distribution of the amount of reflected light is obtained on the basis of the position of the two-dimensional scanning of the laser light and the amount of the reflected light.

9. The method of inspecting a surface-emitting semiconductor laser as defined in claim 1,
wherein the surface-emitting semiconductor laser is an element in the process of formation.

10. The method of inspecting a surface-emitting semiconductor laser as defined in claim 9,
wherein an electrode through which a current is injected into an active layer is not formed in the element.

11. The method of inspecting a surface-emitting semiconductor laser as defined in claim 1, wherein:
the position of the surface-emitting semiconductor laser in a plane parallel to the surface of the semiconductor substrate is confirmed; the surface-emitting semiconductor laser is moved to a predetermined position by moving a test piece stage in a direction parallel to the surface of the semiconductor substrate; and then the laser light irradiation is performed.

12. An inspection device for a surface-emitting semiconductor laser having a resonator which is formed in the vertical direction on a semiconductor substrate,
wherein the surface-emitting semiconductor laser includes a pillar portion in at least a part of the resonator, the pillar portion having an oxidized current blocking layer which has an oxide aperture and an oxidized portion formed around the oxide aperture; and
wherein the inspection device includes:
a test piece stage on which is mounted the surface-emitting semiconductor laser to be inspected;
a movement mechanism which moves the test piece stage in a direction parallel to a surface of the semiconductor substrate to adjust the position of the surface-emitting semiconductor laser in a plane parallel to the surface of the semiconductor substrate;
a laser light source which irradiates the surface-emitting semiconductor laser with laser light from the side on which the pillar portion is disposed in a direction perpendicular to the surface of the semiconductor substrate;
an optical element which focuses the laser light;
a distance adjustment section which adjusts the distance between the surface-emitting semiconductor laser and the optical element;
a scanning section which performs two-dimensional scanning of the laser light reflected by a plane parallel to the surface of the semiconductor substrate; and
a measurement section which measures the amount of reflected light from an object irradiated with the laser light.

13. The inspection device for a surface-emitting semiconductor laser as defined in claim 12,
wherein the measurement section measures the amount of reflected light from the oxide aperture of the oxidized current blocking layer and the amount of reflected light from the oxidized portion of the oxidized current blocking layer.

14. The inspection device for a surface-emitting semiconductor laser as defined in claim 12, further comprising:
an analysis section which obtains a two-dimensional distribution of the amount of reflected light; and
a display section which displays the two-dimensional distribution obtained by the analysis section.

15. The inspection device for a surface-emitting semiconductor laser as defined in claim 13,
wherein the scanning section performs two-dimensional scanning of the laser light reflected by the plane parallel to the surface of the semiconductor substrate, while the distance adjustment section varies the distance between the surface-emitting laser and the optical element, and the distance adjustment section fixes the distance at a point at which the difference between the amount of reflected light from the oxidized portion and the amount of reflected light from the oxide aperture is maximum.

16. The inspection device for a surface-emitting semiconductor laser as defined in claim 12,
wherein the laser light from the laser light source has a wavelength shorter than the wavelength of light emitted by the surface-emitting semiconductor laser.

17. The inspection device for a surface-emitting semiconductor laser as defined in claim 12,
wherein the scanning section performs two-dimensional scanning of the laser light reflected by at least a cross-section of the pillar portion in the plane parallel to the surface of the semiconductor substrate.

18. The inspection device for a surface-emitting semiconductor laser as defined in claim 17,
wherein the scanning section performs two-dimensional scanning of the laser light reflected by a region which is larger than the cross-section of the pillar portion and includes the cross-section of the pillar portion in the plane parallel to the surface of the semiconductor substrate.

19. The inspection device for a surface-emitting semiconductor laser as defined in claim 12,
wherein the surface-emitting semiconductor laser is an element in the process of formation.

20. The inspection device for a surface-emitting semiconductor laser as defined in claim 19,
wherein an electrode through which a current is injected into an active layer is not formed in the element.

21. The inspection device for a surface-emitting semiconductor laser as defined in claim 14,
wherein the analysis section obtains a two-dimensional distribution of the amount of reflected light based on the position of the scanning of the laser light caused by the scanning section and the amount of the reflected light measured by the measurement section.

22. The inspection device for a surface-emitting semiconductor laser as defined in claim 12, further comprising:
a position detection section which confirms the position of the surface-emitting semiconductor laser in the plane parallel to the surface of the semiconductor substrate,
wherein the movement mechanism moves the surface-emitting semiconductor laser to a predetermined position by moving the test piece stage based on information from the position detection section.

* * * * *